US012186519B2

(12) United States Patent
Devich et al.

(10) Patent No.: US 12,186,519 B2
(45) Date of Patent: Jan. 7, 2025

(54) DELIVERY SYSTEM FOR IMPLANTING A MEDICAL DEVICE

(71) Applicant: BIOTRONIK SE & Co. KG, Berlin (DE)

(72) Inventors: Nicholas Devich, Tualatin, OR (US); Eric Austin, Portland, OR (US); Brian M. Taff, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 920 days.

(21) Appl. No.: 17/271,464

(22) PCT Filed: Aug. 13, 2019

(86) PCT No.: PCT/EP2019/071696
§ 371 (c)(1),
(2) Date: Feb. 25, 2021

(87) PCT Pub. No.: WO2020/043481
PCT Pub. Date: Mar. 5, 2020

(65) Prior Publication Data
US 2021/0346706 A1 Nov. 11, 2021

Related U.S. Application Data

(60) Provisional application No. 62/722,999, filed on Aug. 27, 2018.

(51) Int. Cl.
*A61M 39/10* (2006.01)
*A61B 17/34* (2006.01)
(Continued)

(52) U.S. Cl.
CPC ..... *A61M 39/1011* (2013.01); *A61B 17/3468* (2013.01); *A61M 25/0082* (2013.01);
(Continued)

(58) Field of Classification Search
CPC .............. A61N 1/37205; A61N 1/3756; A61N 2001/0578; A61N 2001/058;
(Continued)

(56) References Cited

U.S. PATENT DOCUMENTS 5,261,916 A * 11/1993 Engelson .................. A61F 2/88
606/1
2007/0118079 A1* 5/2007 Moberg ............ A61M 25/0097
604/510

(Continued)

FOREIGN PATENT DOCUMENTS

EP 3125995 B1 5/2018
WO 2017074553 A1 5/2017

OTHER PUBLICATIONS

International Search Report (PCT/ISA/210) and Written Opinion (PCT/ISA/237) mailed on Nov. 11, 2019, by the European Patent Office as the International Searching Authority for International Application No. PCT/EP2019/071696.
(Continued)

*Primary Examiner* — Katherine H Schwiker
*Assistant Examiner* — Zehra Jaffri
(74) *Attorney, Agent, or Firm* — Buchanan Ingersoll & Rooney PC

(57) ABSTRACT

A delivery system for implanting a medical device comprises a delivery catheter having an inner lumen, a mandrel received in the inner lumen of the delivery catheter and movable with respect to the delivery catheter, and an adapter piece connected to the mandrel, wherein the adapter piece, by moving the mandrel with respect to the delivery catheter, is displaceable between a first position in which the adapter piece is received within the inner lumen of the delivery catheter and a second position in which the adapter piece is arranged outside of the inner lumen of the delivery catheter. A tethering member comprises a positive-locking member
(Continued)

adjoining a tether portion, wherein the positive-locking member in a connection state is received on the adapter piece, but is releasable from the adapter piece by displacing the adapter piece from the first position towards the second position.

15 Claims, 11 Drawing Sheets

(51) Int. Cl.
    *A61M 25/00*     (2006.01)
    *A61N 1/372*     (2006.01)
    *A61N 1/375*     (2006.01)

(52) U.S. Cl.
    CPC . *A61N 1/37205* (2013.01); *A61M 2039/1077* (2013.01); *A61N 1/3756* (2013.01)

(58) Field of Classification Search
    CPC ........ A61B 17/3468; A61B 2017/1205; A61B 2017/12054–12068; A61B 2017/1209; A61F 2/95; A61F 2002/9511; A61F 2002/9528; A61F 2002/9534; A61F 2002/9665
    See application file for complete search history.

(56) References Cited

U.S. PATENT DOCUMENTS

| | | | |
|---|---|---|---|
| 2014/0018818 A1* | 1/2014 | Somogyi | A61N 1/372 606/129 |
| 2015/0051611 A1 | 2/2015 | Schmidt et al. | |
| 2015/0051682 A1* | 2/2015 | Schmidt | A61N 1/37205 607/122 |
| 2015/0094735 A1 | 4/2015 | Ward et al. | |
| 2015/0273207 A1 | 10/2015 | Tran et al. | |
| 2017/0312479 A1 | 11/2017 | Keaveney et al. | |
| 2018/0104451 A1 | 4/2018 | Kerns et al. | |
| 2018/0104452 A1* | 4/2018 | Goodman | A61N 1/37512 |
| 2018/0116678 A1* | 5/2018 | Melanson | A61B 17/12181 |
| 2018/0303513 A1* | 10/2018 | Kerns | A61B 17/3468 |

OTHER PUBLICATIONS

Chinese Office Action for Application No. 201980063969.4 dated Aug. 15, 2024.

* cited by examiner

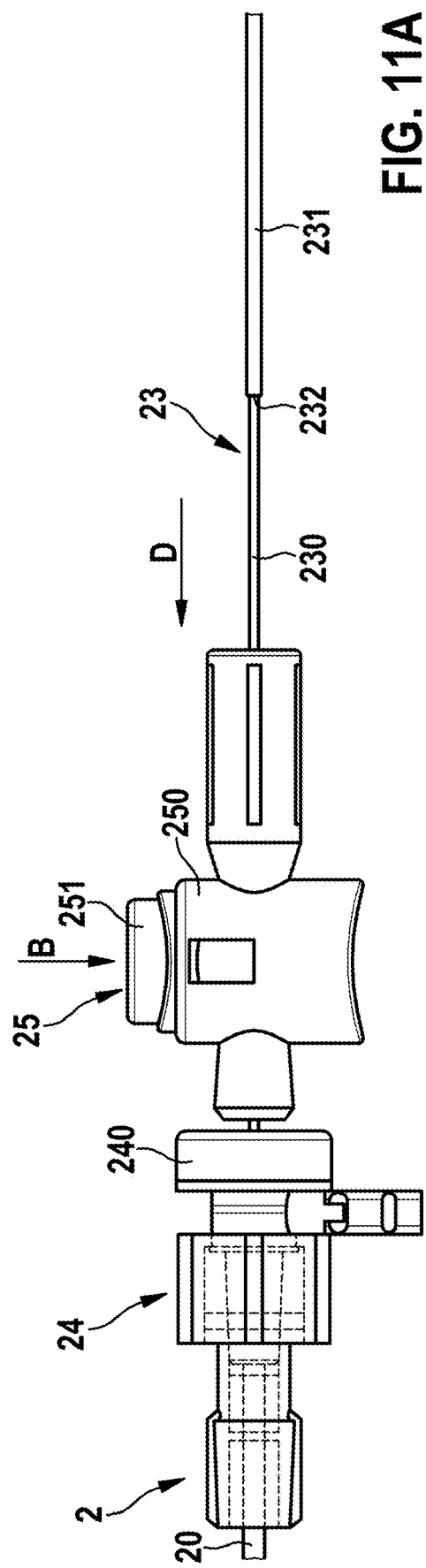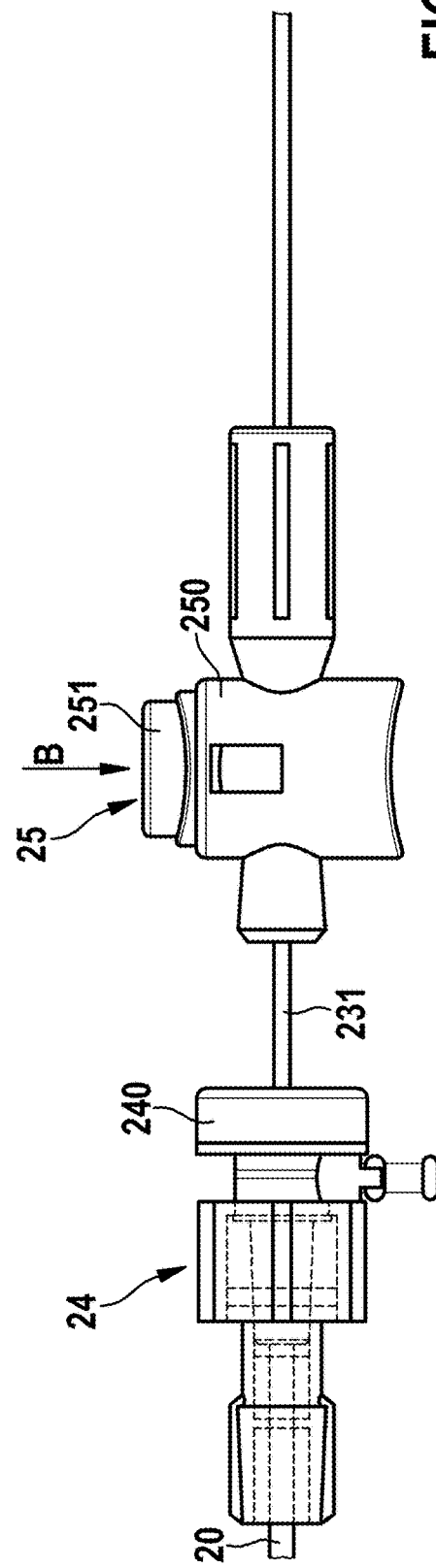

DELIVERY SYSTEM FOR IMPLANTING A MEDICAL DEVICE

CROSS-REFERENCE TO RELATED APPLICATIONS

This application is the United States national phase under 35 U.S.C. § 371 of PCT International Patent Application No. PCT/EP2019/071696, filed on Aug. 13, 2019, which claims the benefit of U.S. Provisional Patent Application No. 62/722,999, filed on Aug. 27, 2018, the disclosures of which are hereby incorporated by reference herein in their entireties.

TECHNICAL FIELD

The present disclosure generally relates to a delivery system for implanting a medical device, to an assembly comprising a delivery system and to a method for releasing a medical device from a delivery system.

BACKGROUND

A delivery system of this kind comprises a delivery catheter which may be advanced into a patient to implant a medical device, such as for example a leadless pacemaker device, in a patient, in particular within the heart of a patient. By means of the delivery catheter an implant location is accessed while the medical device to be implanted is connected to the delivery catheter, and by releasing the medical device from the delivery catheter the medical device may remain at its implant location while the delivery catheter is removed from the patient.

Leadless pacemakers, in contrast to pacemakers implanted subcutaneously using leads extending transvenously into the heart, avoid leads in that the pacemaker device itself is implanted into the heart, the pacemaker having the shape of a capsule for implantation into cardiac tissue, in particular the right ventricular wall of the right ventricle. Such leadless pacemakers exhibit the inherent advantage of not using leads, which can reduce risks for the patient involved with leads transvenously accessing the heart, such as the risk of pneumothorax, lead dislodgement, cardiac perforation, venous thrombosis and the like. Leadless pacemakers may specifically be designed for implantation in the right ventricle and, in this case, during implant are placed in or on the right ventricular wall. A ventricular pacing may for example be indicated in case a dysfunction at the AV node occurs, but the sinus node function is intact and appropriate.

The implanting of for example a leadless pacemaker device to a specific location of the patient's heart requires proper positioning as well as proper anchoring such that the leadless pacemaker device remains in position when implanted. To provide for an anchoring a leadless pacemaker device may for example comprise an arrangement of tines which may engage with cardiac tissue such that the leadless pacemaker device may be fixated with respect to tissue by means of the tines.

During the process of implantation, typically a so-called tug test shall be performed in which a pulling force is exerted on the medical device once it is positioned at an implant location. During such tug test the medical device should be allowed to sit freely such that it is not mechanically biased by the delivery catheter.

Following the tug test, typically an electrical testing is performed in order to ensure that the medical device, for example a leadless pacemaker device, functions correctly and is positioned at a location for proper pacing operation and signal reception. Also during such electrical testing the medical device should sit freely and should not be biased by the delivery catheter such that the electrical testing is not disturbed by the delivery catheter.

Hence, upon positioning a medical device at an implant location, it is necessary to provide for an at least partial detachment of the medical device from the delivery catheter to allow for a tug test and an electrical testing which is unbiased by the delivery system. If, however, in the course of the tug test or during electrical testing it is found that a repositioning of the medical device may be required, the medical device must again be captured and must be implanted at another location. Hence, a full release of the medical device from the delivery system should take place only once the testing is completed and it is found that the medical device is positioned and fixated correctly and in addition functions properly.

The releasing of the medical device from the delivery system herein shall be easy and safe, ensuring that the medical device comes free of the delivery system in order to allow a removal of the delivery system while the medical device properly remains in place at its implant location.

United States Publication No. 2015/0051611 discloses a delivery system for implanting a leadless cardiac pacing device, the delivery system comprising a delivery catheter having an inner lumen in which a retrieval catheter device is received. The retrieval catheter device comprises a snare forming a multiplicity of loops allowing to capture a medical device at a connection member having a mushroom shape.

European Patent No. 3 125 995 discloses a delivery system for a leadless pacemaker device, the delivery system comprising a delivery catheter and a tethering mechanism arranged thereon. The tethering mechanism comprises a tether which extends along the delivery catheter and, at an end of the delivery catheter associated with the medical device, forms a loop which provides for a connection to the medical device. The tether may be pulled through a channel in order to release one end of the tether from the delivery catheter and to in this way open the loop to release the medical device from the delivery catheter.

The present disclosure is directed toward overcoming one or more of the above-mentioned problems, though not necessarily limited to embodiments that do.

SUMMARY

It is an object of the present invention to provide a delivery system for implanting a medical device and a method for releasing a medical device from a delivery system which allow for an implantation of a medical device and the performing of a testing while the medical device is connected to the delivery system, and in addition, in an easy and safe manner, allow for a release of the medical device from the delivery system.

A delivery system according to claim 1, an assembly according to claim 11, and a method for releasing a medical device from a delivery system according to claim 15 are provided.

In one aspect, a delivery system for implanting a medical device comprises a delivery catheter having an inner lumen, a mandrel received in the inner lumen of the delivery catheter, the mandrel being movable with respect to the delivery catheter, and an adapter piece connected to the mandrel. The adapter piece, by moving the mandrel with respect to the delivery catheter, is displaceable between a first position in which the adapter piece is received within the inner lumen of the delivery catheter and a second position in which the adapter piece is arranged outside of the inner lumen of the delivery catheter. The delivery system furthermore comprises a tethering member comprising a tether portion having a first end at which the tethering member is connected to the adapter piece, wherein the tethering member further comprises a positive-locking member adjoining the tether portion at a distance from the first end. The positive-locking member in a connection state is received on the adapter piece and is locked with respect to the adapter piece while the adapter piece is in the first position. The positive-locking member is releasable from the adapter piece by displacing the adapter piece from the first position towards the second position.

The delivery system comprises a delivery catheter having an inner lumen in which a mandrel is received. The mandrel is connected to an adapter piece which, in a first position, is received within the inner lumen of the delivery catheter and can be moved out of the inner lumen to assume a second position by moving the mandrel with respect to the delivery catheter.

The adapter piece serves to control the establishment and release of a connection of a medical device to the delivery system. For this, a tethering member is connected to the adapter piece, the tethering member at a first end being arranged on the adapter piece and carrying, at a distance from the first end, a positive-locking member which releasably may be connected to the adapter piece. In a connection state, in which the positive-locking member is received on the adapter piece, the tethering member by means of its tether portion hence forms a loop, which allows for a connection of a medical device to the delivery system, for example in that the tether portion of the tethering member extends through an opening of a connection member of the medical device such that by means of the tether portion the medical device is fixedly held on the delivery system.

The positive-locking member in the connection state is received on the adapter piece and is locked with respect to the adapter piece while the adapter piece is in the first position and hence is received within the inner lumen of the delivery catheter. The positive-locking member in the connection state is held on the adapter piece in a positive-locking manner such that the fixation of the medical device to the delivery system is locked.

For releasing the medical device from the delivery system, the adapter piece may be moved from its first position towards the second position and hence may slide out of the delivery catheter. When the adapter piece has exited the delivery catheter, the locking of the positive-locking member with respect to the adapter piece is released, such that the positive-locking member may disengage from the adapter piece and the loop previously formed by the tethering member is opened. The medical device hence may be disconnected from the delivery system.

The releasing of the medical device from the delivery system hence is controlled by moving the adapter piece with respect to the delivery catheter. The moving of the adapter piece takes place by actuating a mandrel, the mandrel being connected to the adapter piece such that the adapter piece may be displaced from its first position within the delivery catheter towards the second position in which the adapter piece is placed outside of the delivery catheter.

In one embodiment, the positive-locking member is arranged at a second end of the tether portion opposite the first end at which the tether portion is connected to the adapter piece. The tether portion in between the first end and the second end hence forms a loop if the positive-locking member is received on and is locked with respect to the adapter piece, such that by means of the tether portion a fixed connection of a medical device to the delivery system may be established.

In one embodiment, the positive-locking member comprises a first diameter, when measured along a plane perpendicular to a longitudinal direction of extension of the tethering member, larger than a second diameter of the tether portion. The positive-locking member may for example have a spherical shape and hence provides for a widened diameter at the second end of the tether portion. The positive-locking member, in its connection state, is received on the adapter piece such that it is held on the adapter piece in a positive-locking fashion, the positive-locking member interacting with a suitable counter-portion of the adapter piece such that the positive-locking member cannot be released from the adapter piece, at least not without moving the adapter piece from its first position in which it is received within the delivery catheter to the second position in which it is placed outside of the delivery catheter.

In one embodiment, the adapter piece comprises a body and a retainer groove formed on the body, wherein the tether portion in the connection state of the positive-locking member is received in the retainer groove. The positive-locking member herein may be received in a recess formed on the body of the adapter piece, the recess adjoining the retainer groove. The retainer groove has a width such that the tether portion may be received within the retainer groove, but the diameter of the positive-locking member exceeds the width of the retainer groove such that the positive-locking member cannot be pulled through the retainer groove, hence providing for a fixation of the positive-locking member on the adapter piece.

The retainer groove may extend along a longitudinal direction along which the delivery catheter generally extends and along which the adapter piece is movable within the inner lumen of the delivery catheter. The retainer groove as well as the recess adjoining the retainer groove herein may be opened towards a lateral side, i.e. in a direction transverse to the longitudinal direction defined by the delivery catheter. Hence, the positive-locking member as well as the tether portion may be removed from the adapter piece along the transverse direction by disengaging the positive-locking member from the recess and by removing the tether portion from the retainer groove. However, as the adapter piece in its first position is received within the inner lumen of the delivery catheter, a disengagement of the positive-locking member from the recess is blocked by the delivery catheter, such that the connection of the positive-locking element to the adapter piece is locked. Only upon moving the adapter piece to exit from the delivery catheter the positive-locking element may disengage from the recess of the adapter piece such that the tether portion at its second end is released from the adapter piece and the loop previously formed by the tethering member is opened.

In one embodiment, the adapter piece comprises a slanted face formed on the body at a transition between the recess and the retainer groove, wherein the slanted face is formed such that the positive-locking member is guided to release the tether portion from the retainer groove in case the locking of the positive-locking member with respect to the adapter piece is released and a pulling force is exerted on the tether portion. The slanted face is formed at the transition between the recess and the retainer groove and is inclined with respect to the longitudinal direction of extension of the retainer groove. If a pulling force is exerted on the tether portion when the adapter piece is in its second position outside of the delivery catheter, hence, the positive-locking member may slide up the slanted face such that it comes out of engagement from the recess formed on the body of the adapter piece, such that the connection of the positive-locking member to the adapter piece is released.

In one aspect, the delivery system further comprises a security device operatively connected to the mandrel, the security device being configured to prevent, in a first actuation state, a movement of the mandrel for releasing the positive-locking member from the adapter piece. The security device shall prevent that the mandrel unintentionally is actuated for moving the adapter piece from its first position towards the second position with respect to the delivery catheter. The security device hence shall prevent that the positive-locking member unintentionally is released from the adapter piece, which otherwise may cause an unintentional disengagement of the medical device from the delivery system.

In one embodiment, the security device may comprise an actuation member which is actuatable for transferring the security device from the first actuation state to a second actuation state. In the second actuation state the security device shall allow for a movement of the mandrel such that, by moving the mandrel, the adapter piece can be displaced from the first position towards the second position and hence can be moved with respect to the delivery catheter to exit from the delivery catheter for releasing the positive-locking member from the adapter piece. Hence, an actuation of the mandrel for moving the adapter piece is only possible in case of an actuation of the security device. Only if the actuation member, having for example the shape of a button to be depressed for transferring the security device from the first actuation state to the second actuation state, is actuated, a release of the medical device from the delivery system thus becomes possible.

In one embodiment, the security device comprises a housing body and a blocking opening formed therein. The mandrel is passed through the blocking opening wherein the security device is configured to block a movement of a portion of the mandrel through the blocking opening when the security device is in its first actuation state. Only after transferring the security device into its second actuation state, said portion of the mandrel may be moved through the blocking opening of the security device, such that the mandrel may be moved to exit the adapter piece from the delivery catheter for releasing the positive-locking member from the adapter piece.

The mandrel may in particular comprise a first portion having a rather thin diameter and a second portion adjoining the first portion and having a widened diameter. The security device herein may be configured to allow a passing of the second portion of the mandrel through the blocking opening only when the actuation member is actuated such that the security device assumes the second actuation state.

The tethering member may be formed for example by a cable, suture or wire. The tethering member is generally flexible and hence may be flexibly bendable to form a loop for connecting the medical device to the delivery system. The tethering member may be soft, or may exhibit a substantial firmness (while allowing a sufficient bendability).

The tethering member may be fabricated from a radiopaque material such that the tethering member may be visualized for example in an X-ray examination.

An assembly comprises a delivery system of the kind described above and a medical device having a housing and a connection member arranged on the housing, wherein the tether portion of the tethering member in the connection state of the positive-locking member is connected to the connection member of the medical device. The connection member in particular may comprise an opening through which the tether portion of the tethering member extends when the medical device is connected to the delivery system.

When the positive-locking member is received on the adapter piece and is connected to the adapter piece when the adapter piece is retracted into the delivery catheter, the tethering member forms a loop, the loop providing for a connection of the medical device to the delivery system. The tether portion of the tethering member forming the loop herein interacts with the connection member of the medical device such that an operative connection in between the medical device and the delivery system is established, in particular in that the tether portion extends through an opening formed by the connection member. Once the positive-locking member is released from the adapter piece the tether portion may be pulled out of engagement from the connection member, in particular by passing the positive-locking member through the opening formed by the connection member, such that the medical device is released from the delivery system.

The connection member, in one embodiment, comprises a shaft bordering the opening, wherein the tether portion in the connection state extends about the shaft. The shaft may have a rounded design such that the tether portion slides on a rounded face of the shaft.

In addition, the connection member may comprise a rounded face having, when viewed in a plane perpendicular to a longitudinal axis of the shaft, a convex curvature, the rounded face bordering the opening at a side opposite the shaft. Hence, the opening at the connection member is formed in between rounded faces, which may help to ensure that, when passing the positive-locking member through the opening for releasing the medical device from the delivery system, the positive-locking member may securely slide through the opening without being caught within the opening.

In another aspect, an object is also addressed by a method for releasing a medical device from a delivery system, the method comprising: providing the delivery system in a state in which the medical device is connected to the delivery system, the delivery system comprising a delivery catheter having an inner lumen, a mandrel received in the inner lumen of the delivery catheter and an adapter piece connected to the mandrel, wherein the adapter piece, by moving the mandrel with respect to the delivery catheter, is displaceable between a first position in which the adapter piece is received within the inner lumen of the delivery catheter and a second position in which the adapter piece is arranged outside of the inner lumen of the delivery catheter, wherein the delivery system further comprises a tethering member comprising a tether portion having a first end at which the tethering member is connected to the adapter piece and a positive-locking member adjoining the tether portion at a distance from the first end, wherein the positive-locking member in a connection state is received on the adapter piece and is locked with respect to the adapter piece while the adapter piece is in the first position, wherein the tether portion of the tethering member in the connection state is connected to a connection member of the medical device; and releasing the positive-locking member from the adapter piece by displacing the adapter piece from the first position towards the second position by moving the mandrel for disconnecting the medical device from the tether portion.

The advantages and advantageous embodiments described above for the delivery system and the assembly of a medical device and a delivery system equally apply also to the method such that it, in this respect, shall be referred to the above.

Additional features, aspects, objects, advantages, and possible applications of the present disclosure will become apparent from a study of the exemplary embodiments and examples described below, in combination with the Figures and the appended claims.

BRIEF DESCRIPTION OF THE DRAWINGS

The various features and advantages of the present invention may be more readily understood with reference to the following detailed description and the embodiments shown in the drawings. Herein.

FIGS. 11A-B show views of a security device operatively connected to a mandrel for preventing an unintentional actuation;

DETAILED DESCRIPTION

Figure 1:
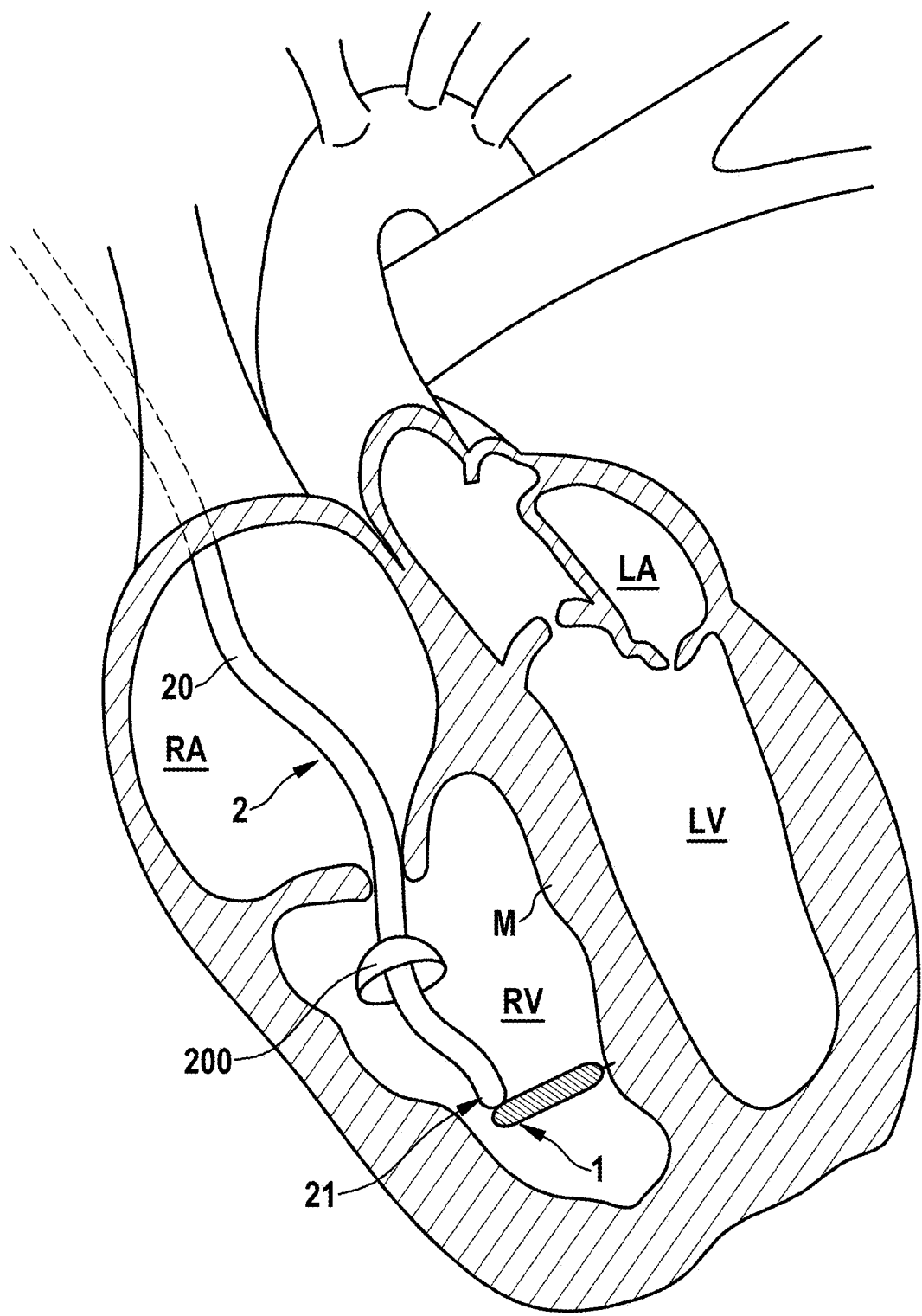
FIG. 1 shows a schematic view of the human heart.

Subsequently, embodiments of the present invention shall be described in detail with reference to the drawings. In the drawings, like reference numerals designate like structural elements.

It is to be noted that the embodiments are not limiting for the present invention, but merely represent illustrative examples.

FIG. 1 shows, in a schematic drawing, a human heart comprising a right atrium RA, a right ventricle RV, a left atrium LA and a left ventricle LV, an implantable medical device 1 being implanted into the right ventricle RV, the implantable medical device 1 for example having the shape of a leadless pacemaker device for providing a pacing of the heart's activity at the right ventricle RV.

For implantation the implantable medical device 1 by means of a delivery system 2 is placed at an implant location, for example in the right ventricle RV—as illustrated in FIG. 1—such that it comes to rest on myocardial tissue M.

Figure 2:
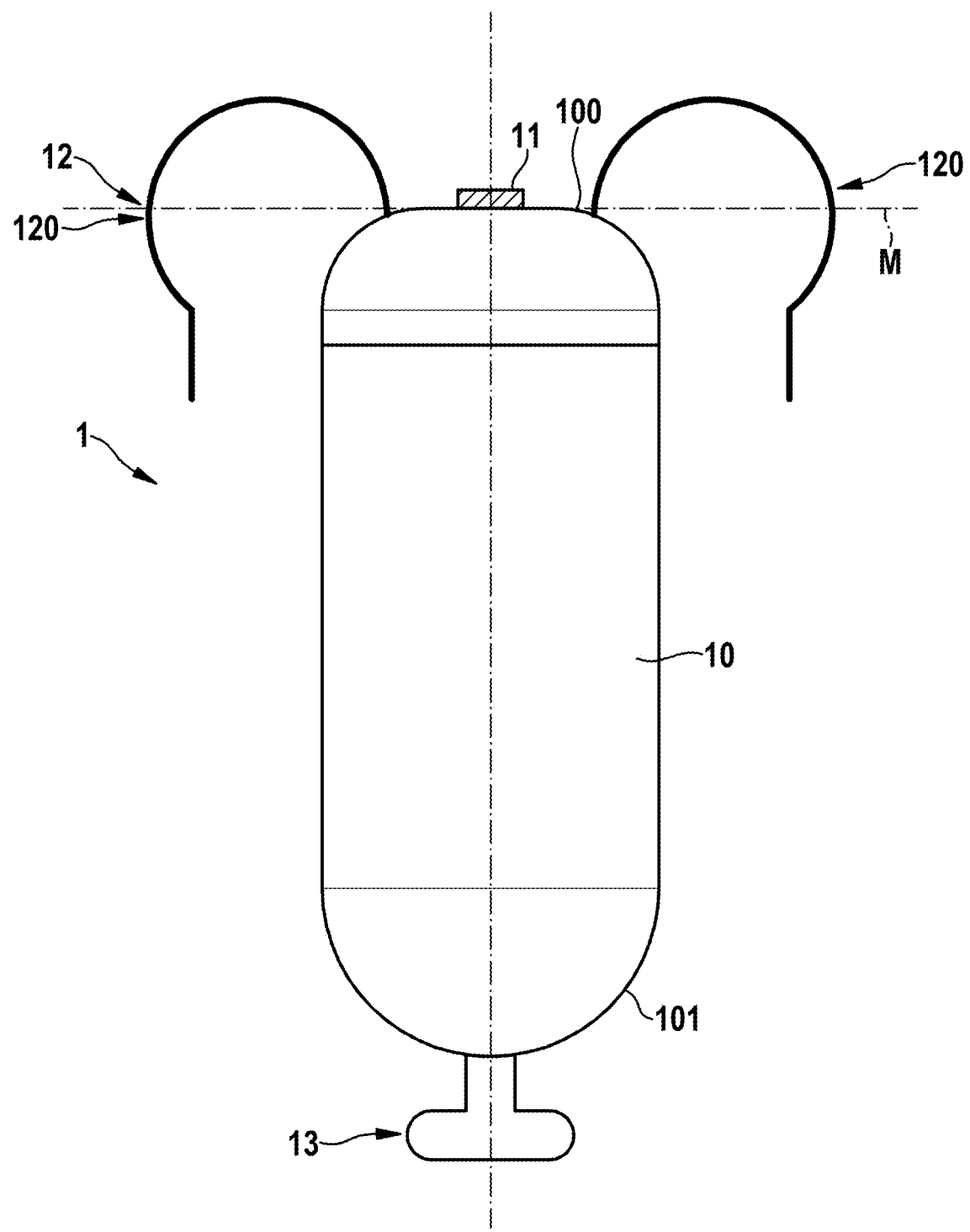
FIG. 2 a schematic view of a leadless pacemaker device to be implanted in a patient's heart.

FIG. 2 shows, in a schematic drawing, an example of an implantable medical device 1 in the shape of a leadless pacemaker device, the implantable medical device 1 having a housing 10 forming a proximal end 101 and a distal end 100, the implantable medical device 1 being configured to be placed on myocardial tissue M by means of its distal end 100. On the distal end 100, herein, an electrode device 11 is placed which, potentially together with other electrodes of the implantable medical device 1, serves to provide for a pacing action in order to stimulate cardiac activity in a defined manner.

During implantation the implantable medical device 1 is to be placed at an implant location, for example on myocardial tissue M, and is to be fastened to tissue at the implant location. For this, the implantable medical device 1 comprises an anchoring device 12 having a multiplicity of anchoring members 120 in the shape of tines, wires, sheets or tubes or the like, the anchoring members 120 extending from the housing 10 of the implantable medical device 1 at the distal end 100 in order to engage with tissue for fastening the implantable medical device 1 to the tissue.

For implantation the implantable medical device 1 is to be delivered towards the implant location by means of a delivery system 2, the delivery system 2 comprising a delivery catheter 20 which is guided for example through the superior vena into the patient's heart to access, via the right atrium RA, the right ventricle RV. During delivery the implantable medical device 1 is fixed to the delivery catheter 20, but is to be released once the implantable medical device 1 has reached the implant location and is fixed to tissue in the region of the implant location.

When the implantable medical device 1, by means of its distal end 100, is placed on tissue at the implant location, the anchoring members 120 of the anchoring device 12 come into engagement with the tissue such that the medical device 1 is mechanically fixed to the tissue. Herein, once the medical device 1 is placed on the tissue at the implant location, a testing is to be performed in order to ensure the mechanical fixation of the medical device 1 to the tissue and in addition to test the proper functionality of the medical device 1, in particular for performing a pacing operation for example in the right ventricle RV of the patient's heart.

Figure 3:
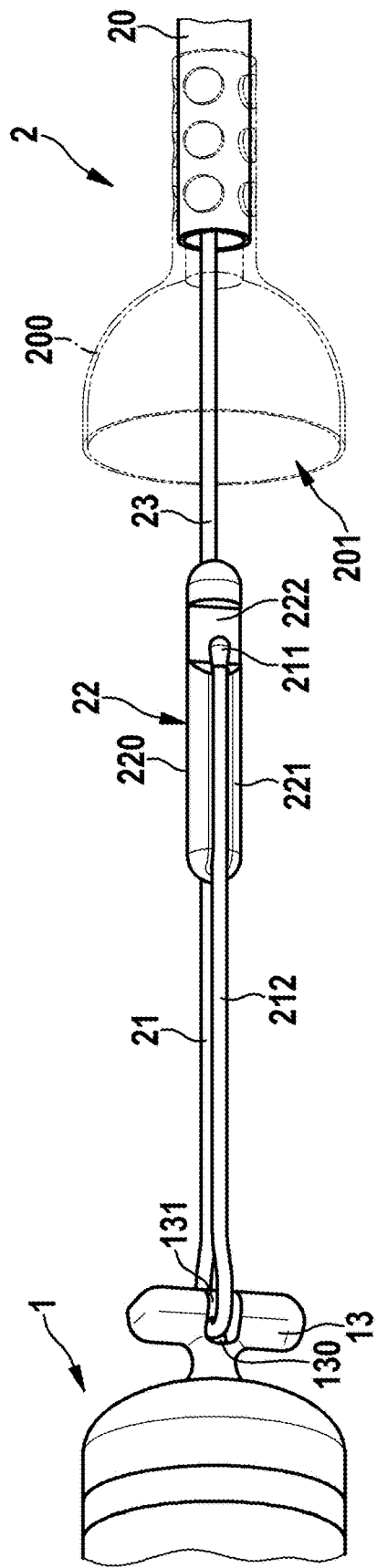
FIG. 3 shows a perspective view of an embodiment of a delivery system for implanting a medical device, in particular a leadless pacemaker device.
Figure 4:
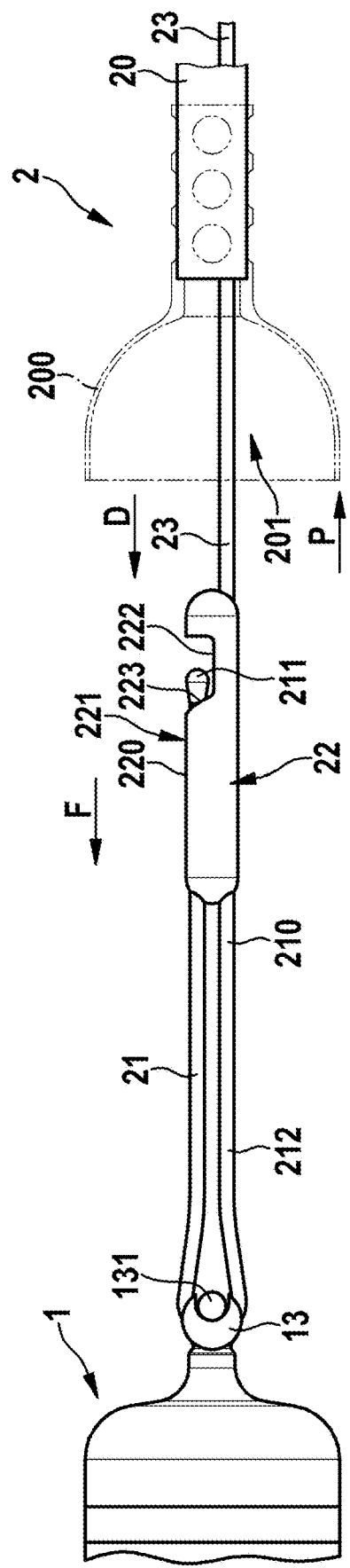
FIG. 4 shows a side view of the arrangement of FIG. 3.

Referring now to FIGS. 3 and 4, an embodiment of a delivery system 2 comprises a delivery catheter 20 generally extending along a longitudinal direction, but being flexible such that the delivery catheter 20 can be guided through body regions of a patient to access for example the patient's heart.

The delivery catheter 20 comprises an inner lumen 201 in which, in the illustrated embodiment, a mandrel 23 is received, the mandrel 23 extending through the entire length of the delivery catheter 20 towards a hand piece at a proximal end of the delivery catheter 20. The mandrel 23 is sufficiently flexible such that it may be deformed together with the delivery catheter 20 when guiding the delivery catheter 20 through body portions of the patient, but at the same time is flexurally rigid and kink-proof such that it may be axially moved with respect to the delivery catheter 20.

The delivery system 2 furthermore comprises an adapter piece 22 fixedly connected to the mandrel 23, for example by welding. The adapter piece 22 has a generally longitudinal shape with rounded tips and is designed such that it may be received within the inner lumen 201 of the delivery catheter 20 when it is retracted into the delivery catheter 20 by means of the mandrel 23.

The adapter piece 22 is part of a tethering mechanism comprising a tethering member 21, which at an end 210 is fixedly connected to the adapter piece 22, for example by welding. The tethering member 21 has a tether portion 212 extending from the adapter piece 22 and, at an end opposite to the end 210, is adjoined by a positive-locking member 211 in the shape of a spherical ball, as visible from FIGS. 3 and 4.

In a connection state, the positive-locking member 211 is received within a recess 222 formed on a body 220 of the adapter piece 22. In the connection state, herein, the tether portion 212 is received within a retainer groove 221 adjoining the recess 222, the retainer groove 221 having a width such that the tether portion 212 may be snuggly placed within the retainer groove 221, but the positive-locking member 211 having a wider diameter is prevented from passing through the retainer groove 221.

The tethering member 21 serves to establish a connection in between a medical device 1 to be implanted and the delivery system 2. In the connection state the positive-locking member 211 at the far end of the tether portion 212 of the tethering member 21 is received in the recess 222 of the adapter piece 22, and by retracting the adapter piece 22 into the inner lumen 201 of the delivery catheter 20 the form locking connection in between the adapter piece 22 and the positive-locking member 211 is locked.

Figure 10:
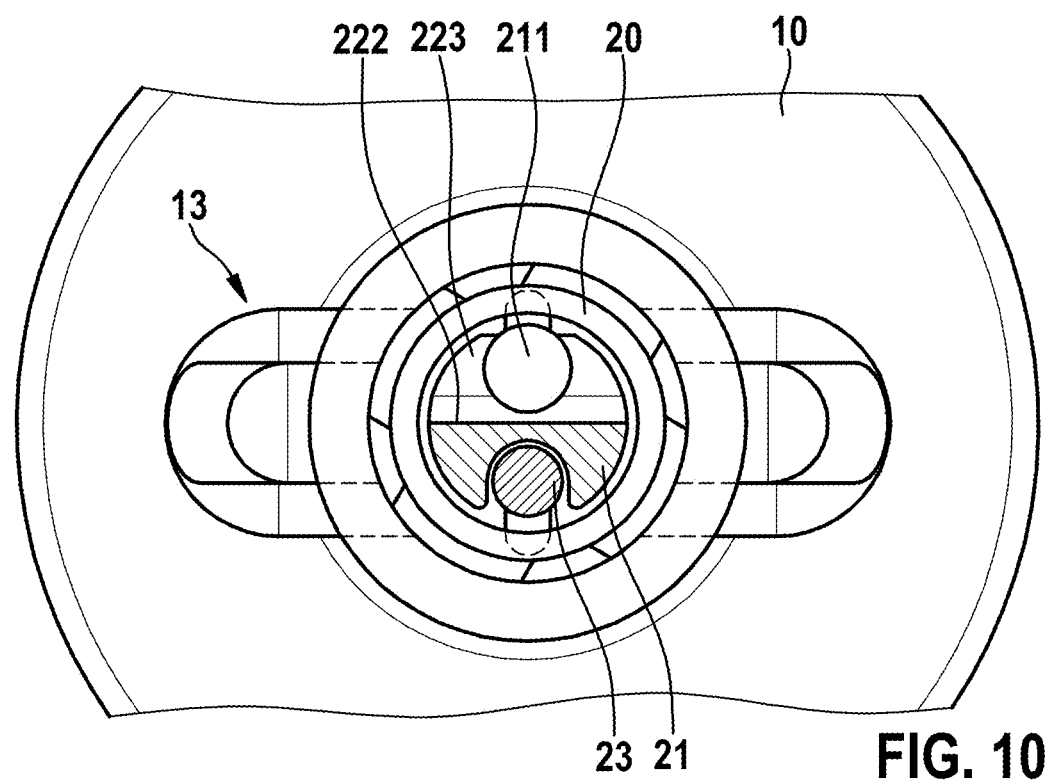
FIG. 10 shows a view of an adapter piece of the delivery system in a position in which it is received within a delivery catheter.

This is illustrated in FIG. 10. In a position in which the adapter piece 22 is received within the inner lumen 201 of the delivery catheter 20 the circumferential wall of the delivery catheter 20 surrounds the adapter piece 22, such that a transverse movement of the positive-locking member 211 to disengage from the recess 222 of the adapter piece 22 is prevented and the connection in between the positive-locking member 211 and the adapter piece 22 is thus locked.

When the positive-locking member 211 is received on the adapter piece 22 and when the adapter piece 22 is retracted into the inner lumen 201 of the delivery catheter 20, the tether portion 212 of the tethering member 21 forms a loop which extends through an opening 130 formed on a connection member 13 of the implantable medical device 1, as this is illustrated in FIGS. 3 and 4. By means of the tethering member 21, hence, a connection in between the delivery system 2 and the medical device 1 is established, such that the medical device 1 by means of the delivery system 2 may be advanced towards an implant location and may be placed on tissue in the region of the implant location.

In a delivery state, herein, the adapter piece 22 is retracted into the delivery catheter 20 in a proximal direction P as indicated in FIG. 4 such that the medical device 1 is drawn towards an end cap 200 fixedly connected to the delivery catheter 20, such that the medical device 1 is received on the end cap 200. Hence, a firm connection in between the medical device 1 and the delivery catheter 20 is established. In this delivery state the medical device 1 by means of the delivery system 2 may be advanced towards an implant location of interest.

Once the medical device 1 has reached the implant location and, by means of the anchoring device 12, has engaged with tissue at the implant location, the medical device 1 shall be released from the delivery system 2. The release herein shall take place in phases in order to, in an initial release phase, allow for a testing on the medical device 1 and, in a second release phase, then fully release the medical device 1 from the delivery system 2 such that the delivery system 2 may be removed while the medical device 1 remains at the implant location.

In the initial release phase, the adapter piece 22 is moved, within the inner lumen 201 of the delivery catheter 20, in a distal direction D as illustrated in FIG. 4, such that the tether portion 212 exits from the delivery catheter 20 while the adapter piece 22 still remains within the inner lumen 201 of the delivery catheter 20. The medical device 1 hence is spatially removed from the end cap 200 of the delivery catheter 20, while the connection via the tethering member 21 still remains in effect.

In this initial release phase a so-called tug test may be performed by pulling on the medical device 1 in order to ensure a proper fixation of the medical device 1 on tissue by means of the anchoring device 12. Such tug test may for example be performed by moving the mandrel together with the adapter piece 22 in the proximal direction P. In addition, an electrical testing of the functionality of the medical device 1, for example a leadless pacemaker device, may be performed to ensure a proper functionality of the medical device 1.

If during this testing it is found that the medical device 1 does not securely hold on the tissue, but is released when applying a defined force during the tug test, or if it is found that the medical device 1 is not positioned correctly for performing its electrical functioning, the medical device 1 may have to be repositioned. For this, the adapter piece 22 may again be retracted into the delivery catheter 20 by pulling the mandrel 23 and together with the mandrel 23 the adapter piece 22 in the proximal direction P such that the medical device 1 again comes to engage with the end cap 200. The medical device 1 may then be positioned at another location, and testing may be repeated until a proper positioning and functioning of the medical device 1 is confirmed.

Once it is found that the medical device 1 is properly implanted and fixed on tissue and in addition functions correctly, the medical device 1 is to be released from the tethering member 21. For this, the adapter piece 22 is, by pushing on the mandrel 23 in the distal direction D, moved out of the inner lumen 201 of the delivery catheter 20, as this is shown in FIGS. 3 and 4. In such position of the adapter piece 22 the positive-locking member 211 on the far end of the tether portion 212 no longer is blocked within the recess 222 formed on the body 220 of the adapter piece 22, such that the positive-locking member 211 may be released from the adapter piece 22 and the loop formed by the tethering member 22 may hence be opened.

The releasing of the positive-locking member 211 from the adapter piece 22 herein is supported by a slanted face 223 at the transition of the recess 222 and the retainer groove 221, as this is apparent from FIG. 4. When exerting a pulling force F on the tether portion 212 the positive-locking member 211 may slide up the slanted face 223 and may hence disengage from the recess 222, such that also the tether portion 212 comes out of engagement from the retainer groove 221. The tether portion 212 at its far end hence is released from the adapter piece 22.

Figure 5:
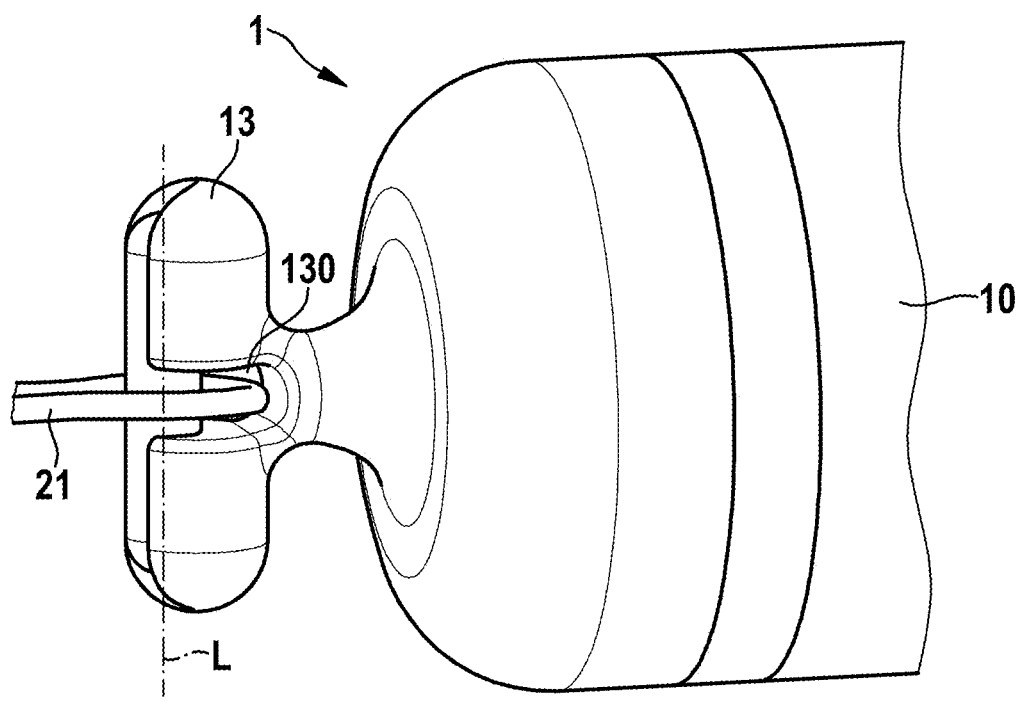
FIG. 5 shows a view of a medical device having a connection member for establishing a connection to a tethering member of the delivery system.
Figure 6A:
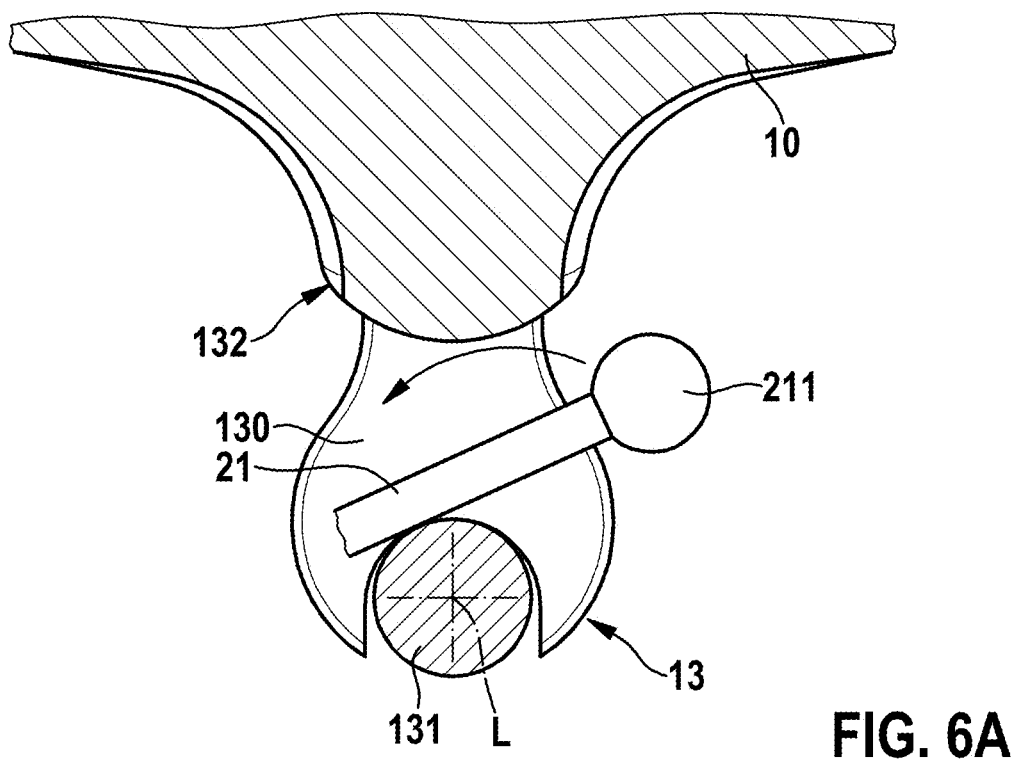
FIGS. 6A-C show cut views of the connection member of the medical device while pulling a tether portion of the tethering member through an opening formed by the connection member for releasing the connection in between the medical device and the delivery system.
Figure 6B:
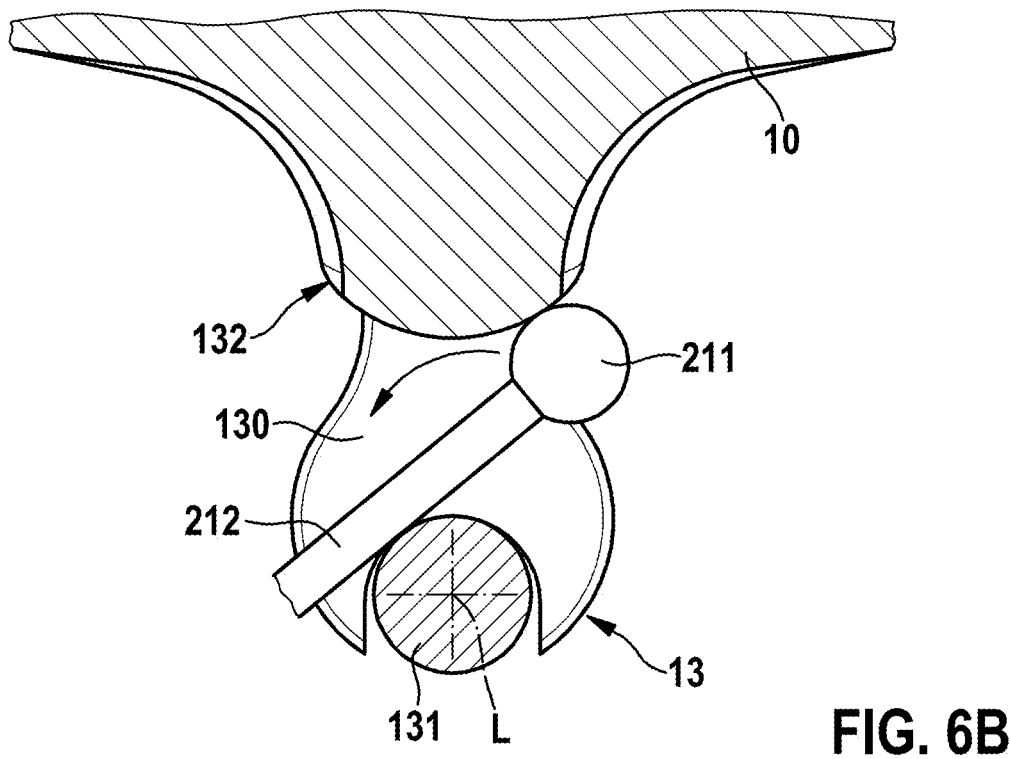
Figure 6C:
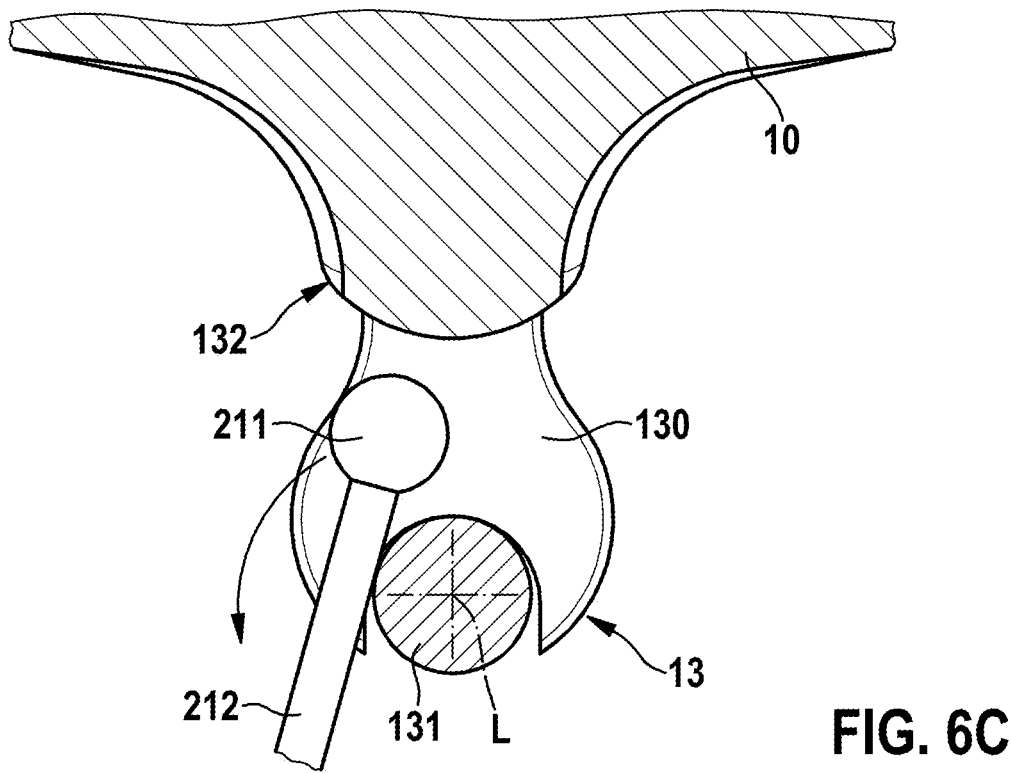
Figure 7A:
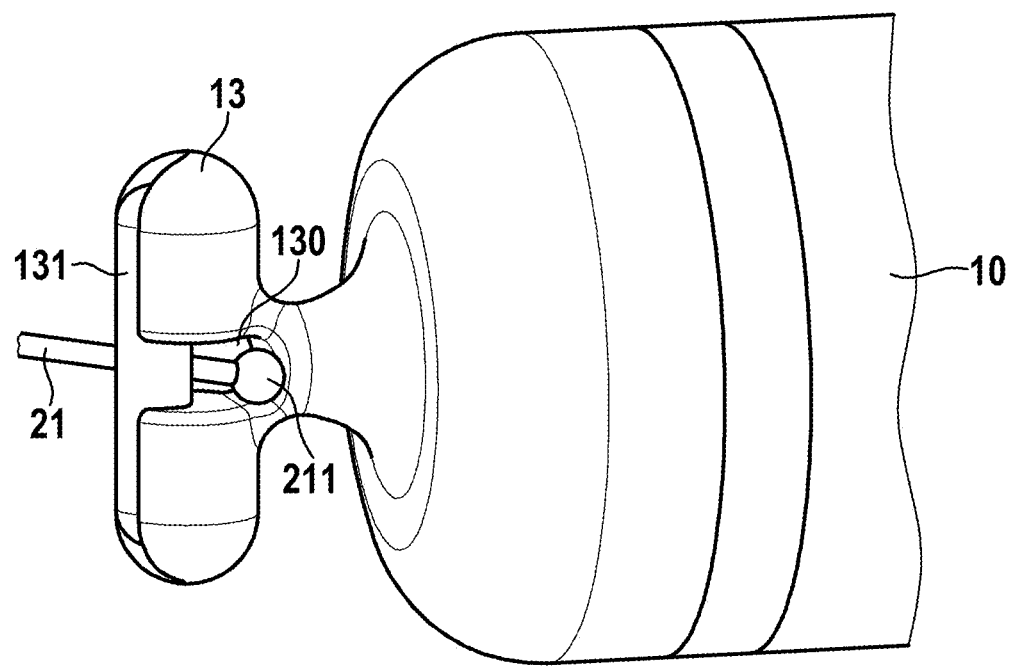
FIGS. 7A-C show perspective views of the connection member of the medical device while pulling the tether portion of the tethering member through the opening formed by the connection member.
Figure 7B:
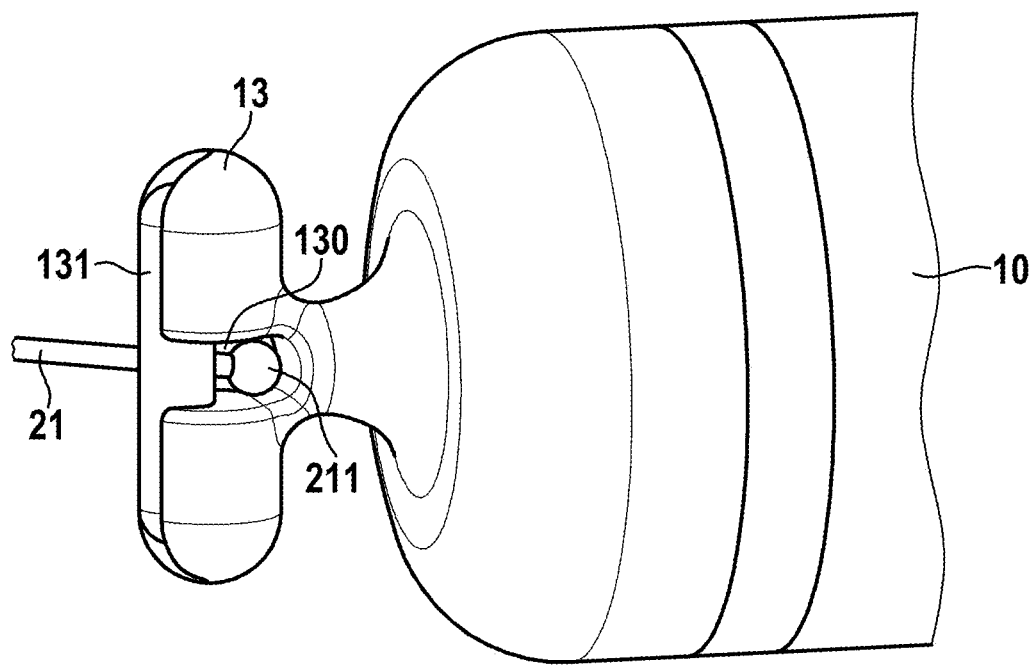
Figure 7C:
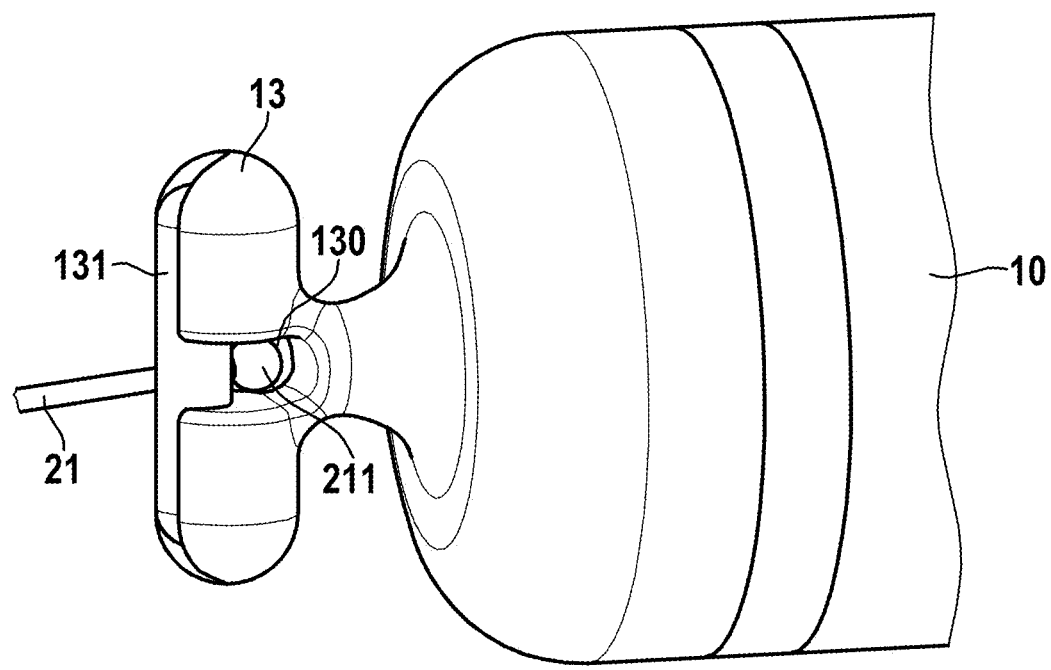

In the connection state, the tether portion 212 extends through an opening 130 of the connection member 13 of the medical device 1, as this is illustrated in FIG. 5. When the positive-locking member 211 is to be released from the adapter piece 22, the tethering member 21 may be pulled through the opening 130 to disconnect from the connection member 13, as illustrated in FIGS. 6A to 6C and 7A to 7C. In particular, when pulling on the tethering member 21 the positive-locking member 211 is passed through the opening 130 of the connection member 13 and is moved around a shaft 131 of the connection member 13 about which the tether portion 212 extends in the connection state.

Once the positive-locking member 211 is passed through the opening 130, the medical device 1 is free of the tethering member 21 and the connection in between the delivery system 2 and the medical device 1 is fully released.

As visible from FIGS. 6A to 6C and 7A to 7C, the shaft 131 extending along a longitudinal axis L is rounded. In addition, the opening 130 at a side opposite to the shaft 131 is bordered by a rounded face 132 having a convex curvature, when viewed along a plane perpendicular to the longitudinal axis L. Because the opening 130, hence, is bordered, in the plane perpendicular to the longitudinal axis L of the shaft 131, by rounded faces, the positive-locking member 211 may safely pass through the opening 130, at a minimum risk of being caught within the opening 130.

For pulling the tethering member 21 through the opening 130, the mandrel 23 together with the adapter piece 22 is moved in the proximal direction P into the delivery catheter 20. Once the connection to the medical device 1 is fully released, the delivery catheter 20 may be removed from the patient.

The tethering member 21 may be made of a radiopaque material such that the positioning of the tethering member 21 may be visualized by an X-ray technology during implant.

In the embodiment of the connection member 13 of the medical device 1 of FIG. 5 and FIGS. 6A to 6C, 7A to 7C, the shaft 131 is for example received within a slot at a distal face of the connection member 13 and is welded to the connection member 13 within the slot. In the connected state the tether portion 212 of the tethering member 221 extends about the shaft 131 such that the medical device 1 is fixedly connected to the delivery system 2.

Figure 8:
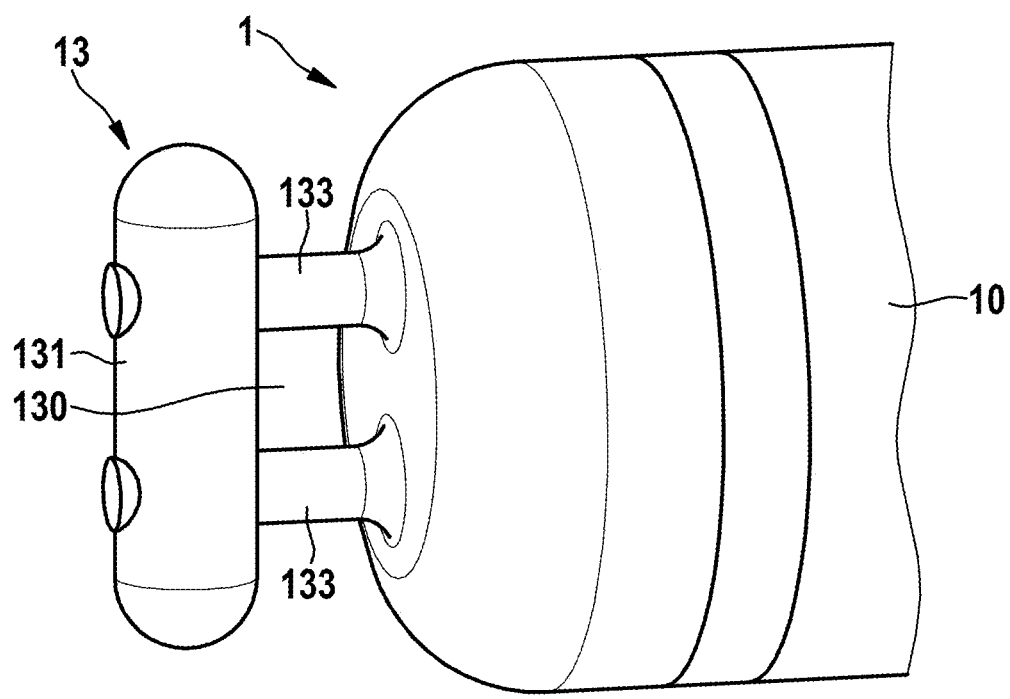
FIG. 8 shows a view of another embodiment of a connection member of a medical device.

In another embodiment shown in FIG. 8, a shaft 131 is connected to a housing 10 of the medical device 1 by means of two posts 133, the opening 130 being formed in between the posts 133 and being bordered by the shaft 131. The posts 133, in the embodiment of FIG. 8, engage with mounting openings of the shaft 131 and are for example welded to the shaft 131.

Figure 9:
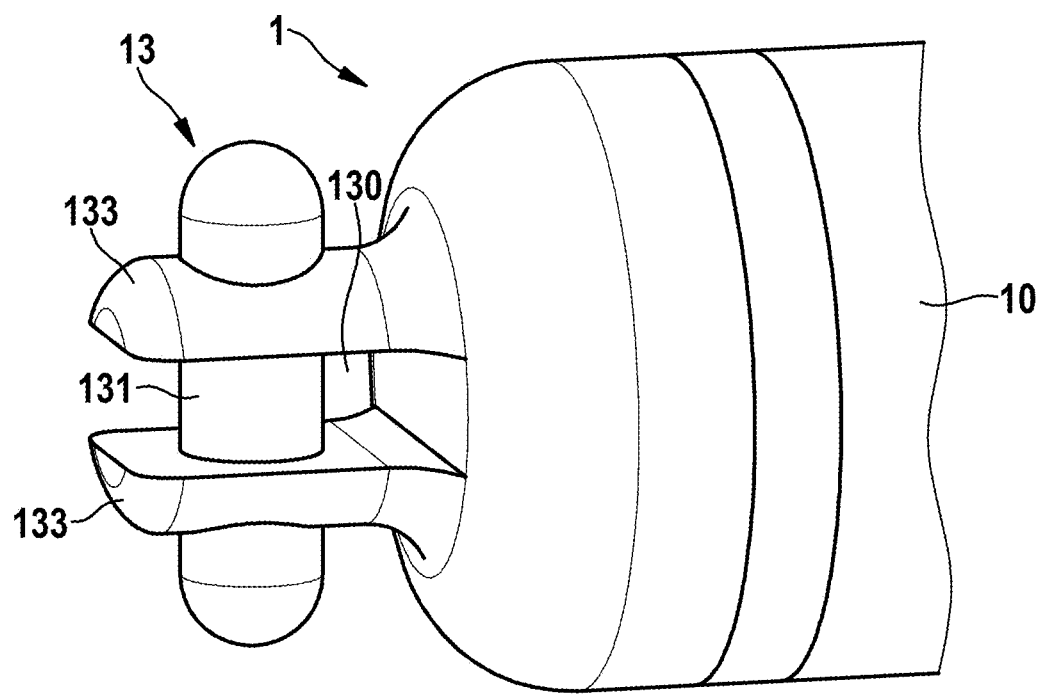
FIG. 9 shows a view of yet another embodiment of a connection member of a medical device.

In a different embodiment shown in FIG. 9, a shaft 131 is received within mounting openings of two posts 133 projecting distally from the housing 10 of the medical device 1, the opening 130 again being formed in between the posts 133 and being bordered by the shaft 131.

Referring now to FIG. 10, in a position in which the adapter piece 21 is retracted into the delivery catheter 20 the adapter piece 21 is snugly received within the inner lumen 201 of the delivery catheter 20. The positive-locking member 211 received within the recess 222 formed on the body 220 of the adapter piece 22 hence is blocked and prevented to disengage from the recess 222, such that a positive-locking connection in between the adapter piece 22 and the positive-locking member 211 on the tether portion 212 is established. By moving the adapter piece 22 in the distal direction D out of the inner lumen 201 of the delivery catheter 20, the blocking of the positive-locking member 211 within the recess 222 is released, such that the positive-locking member 211 can disengage from the recess 222 for disconnecting the delivery system 2 from the medical device 1.

Referring now to FIGS. 11A, 11B and 12A, 12B, the delivery catheter 20, at a proximal end, is connected to a hand piece 24 through which the mandrel 23 is guided into the delivery catheter 20. The hand piece 24 may be actuatable to cause for example a deflection of the delivery catheter 20 in order to facilitate a guiding of the delivery catheter 20 towards an implant location for delivering the medical device 1.

The mandrel 23 enters the hand piece 24 at a valve element 240. In order to prevent an unintentional actuation of the mandrel 23, a security device 25 is placed on the mandrel 23, the security device 25 being configured to prevent, in a delivery state of the delivery system 2, that the mandrel 23 may be pushed into the delivery catheter 20 in the distal direction D, by which movement otherwise the adapter piece 22 may be caused to exit from the delivery catheter 20 allowing the positive-locking element 211 hence to disengage from the adapter piece 22.

Figure 12B:
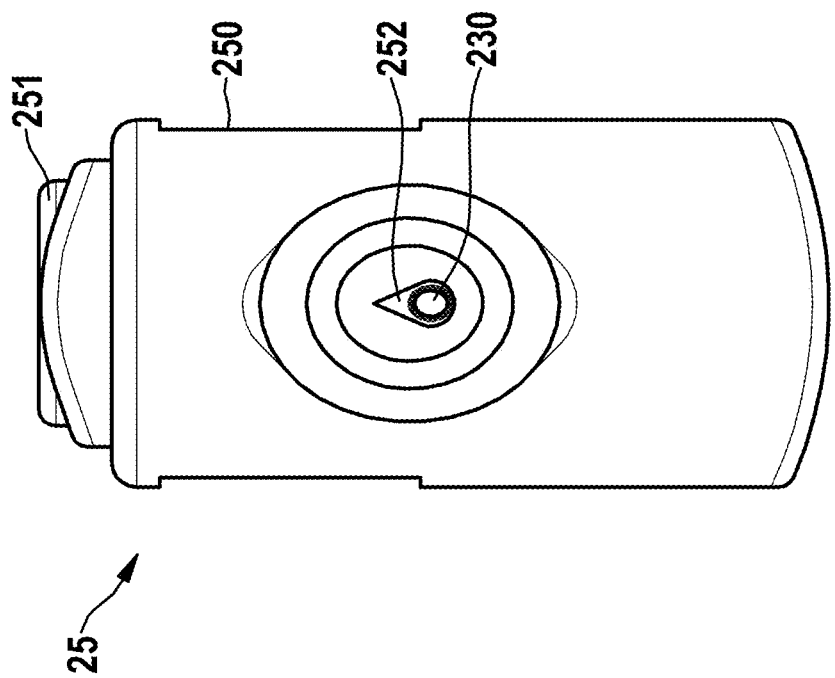
FIGS. 12A-B show views of the security device in different actuation states.
Figure 12A:
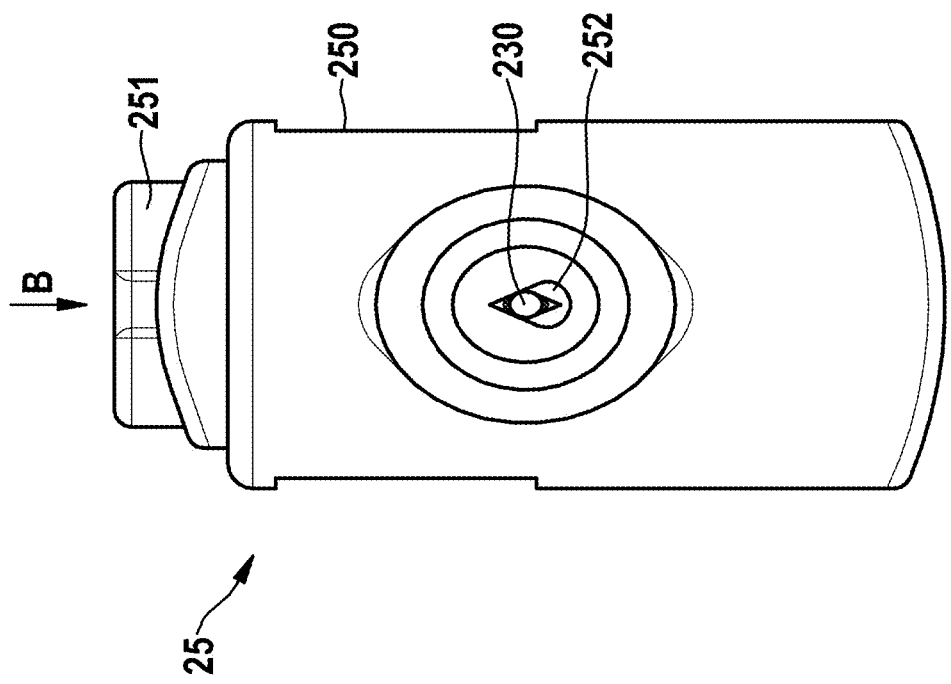

The security device 25 comprises a housing 250 forming a blocking opening 252 through which the mandrel 23 is passed, as this is apparent from FIGS. 12A and 12B. The blocking opening 252 has an asymmetrical shape formed by a narrowed portion at the top (when viewing FIGS. 12A and 12B) and a widened portion at the bottom. The mandrel 23 comprises different portions, namely a thin portion 230 having a small cross-sectional diameter and a widened portion 231 having an increased diameter as compared to the thin portion 230, a step 232 being formed in between the different portions 230, 231 as schematically indicated in FIG. 11A. The mandrel 23 is operatively connected to an actuation member 251 which is actuatable along an actuation direction B with respect to the housing 250, such that by actuating the actuation member 251 the mandrel 23 is movable within the blocking opening 252, as apparent from FIGS. 12A and 12B.

During a delivery state in which the medical device 1 is fixedly connected to the delivery system 2 by means of the tethering member 21, the mandrel 23 with its thin portion 230 passes through the blocking opening 252, as this is illustrated in FIG. 12A. Because the thin portion 230 of the mandrel 23 is received in the narrow portion of the blocking opening 252, the mandrel 23 can be advanced in the distal direction D with respect to the security device 25 only until the wider portion 231 at the step 232 abuts housing portions surrounding the blocking opening 252, such that a further advancement of the mandrel 23 in the distal direction D is prevented.

The security device 25 in combination with the mandrel 23 is designed such that the mandrel 23 can be moved in the distal direction D with respect to the delivery catheter 20 only such far that the adapter piece 22 at the distal end of the delivery catheter 20 cannot exit from the delivery catheter 20. By means of the security device 25 hence a release of the positive-locking member 211 from the adapter piece 22 is prevented.

By actuating the actuation member 251 the mandrel 23 is transversely displaced within the blocking opening 252, as illustrated in FIG. 12B, such that the mandrel 23 comes to rest in the widened portion of the blocking opening 252. The mandrel 23 hence, by means of its widened portion 231, may be passed through the blocking opening 252, such that the mandrel 23 may be advanced—as illustrated in FIG. 11B—further in the distal direction D through the delivery catheter 20 to cause the adapter piece 22 to exit from the delivery catheter 20 for releasing the medical device 1 from the delivery system 2.

Upon actuation of the actuation member 251 for transferring the security device 25 into the second state, the security device 25 may fully be removed from the mandrel 23 at the proximal end of the delivery system 2.

Figure 13A:
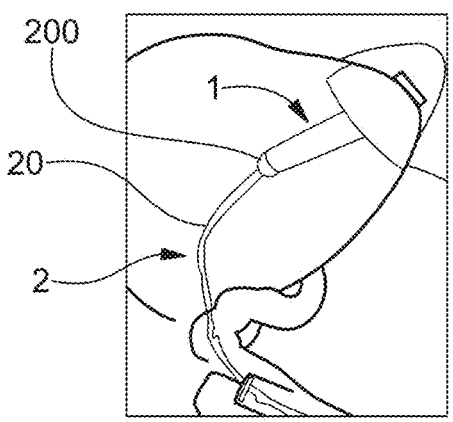
FIGS. 13A-E show different views while implanting a medical device using a delivery system.
Figure 13B:
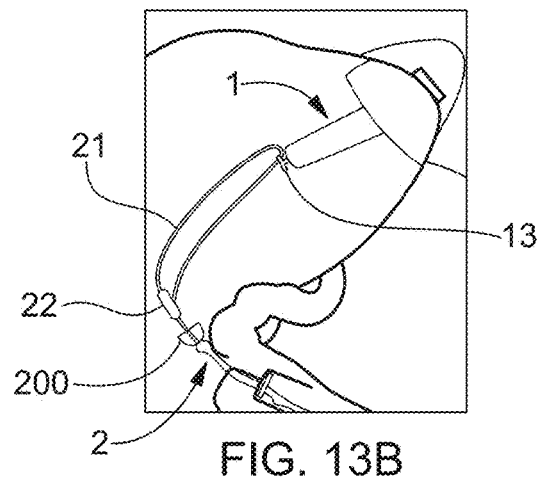

FIGS. 13A to 13B illustrate an example of an implantation process.

In a delivery state, as illustrated in FIG. 13A, the medical device 1 is received on the end cap 200 of the delivery catheter 20 and, by means of the tethering mechanism comprised of the tethering member 21, the adapter piece 22 and the mandrel 23, is fixedly connected to the delivery catheter 20. In this delivery state the medical device 1 may be advanced towards an implant location and may be placed on tissue in the region of the implant location.

Once the implant location is reached and the medical device 1 is placed on tissue in the region of the implant location, as illustrated in FIG. 13B, the adapter piece 22 is moved distally in the delivery catheter 20 such that the tethering member 21 exits from the delivery catheter 20 while the adapter piece 22 still remains within the delivery catheter 20. The medical device 1 hence is spatially removed from the end cap 200 of the delivery catheter 20. In this state the medical device 1 is allowed to sit freely on tissue in the region of the implant location, allowing to perform a tug test and an electrical testing of the medical device 1.

Figure 13C:
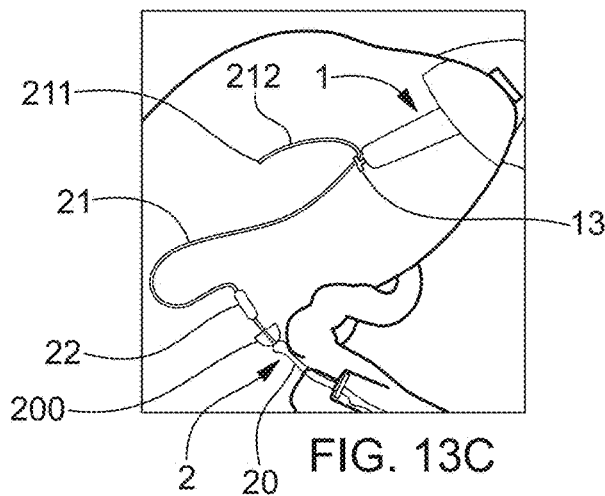

Once the testing has successfully been concluded, the adapter piece 22 is further advanced in the distal direction D by moving the mandrel 23 until the adapter piece 22 exits from the delivery catheter 20, as this is illustrated in FIG. 13C. In this state the positive-locking member 211 at the far end of the tether portion 212 of the tethering member 21 becomes free of the adapter piece 22.

Figure 13D:
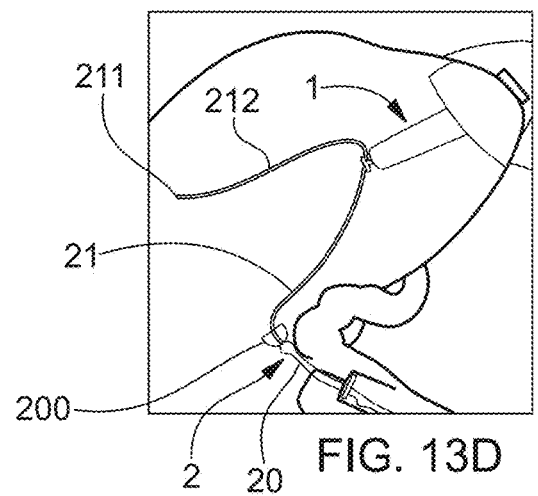

By now retracting the adapter piece 22 in the proximal direction P into the delivery catheter 20, as illustrated in FIG. 13D, the tethering member 21 is pulled in the proximal direction P such that the positive-locking member 211 is pulled through the opening 130 of the connection member 13 of the medical device 1.

Figure 13E:
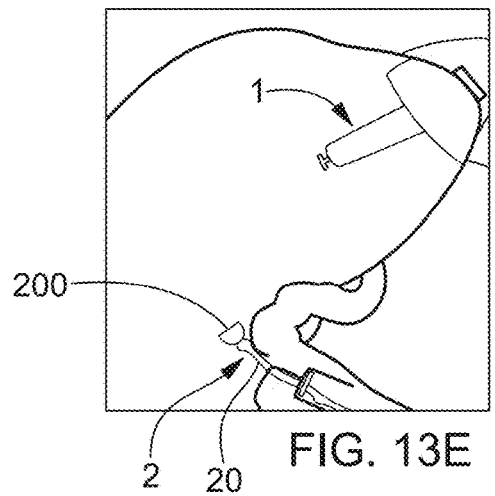

In a release state, shown in FIG. 13E, the medical device 1 is free of the delivery system 2, such that the delivery system 2 may be removed while the medical device 1 remains in place at the implant location.

By using a tethering member of the kind as described above a fixed connection between the delivery system and the medical device in a delivery state may be established, wherein the tethering member may be soft or may have a substantial firmness. The connection herein is established by a loop formed by the tethering member, wherein the loop may be opened to release the medical device from the delivery system.

By using a tethering member the medical device may be allowed to sit freely in an initial release phase, allowing for a reliable testing, such as performing a tug test or a testing for a suitable electrical functioning.

The design of the tethering mechanism allows for an easy recapturing if, during testing, it is found that a repositioning of the medical device is indicated.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range, including the end points.

LIST OF REFERENCE NUMERALS

1 Leadless pacemaker device
10 Housing
100 Distal end
101 Proximal end
11 Electrode
12 Anchoring device
120 Anchoring member
13 Connection member
130 Opening
131 Shaft
132 Rounded face
133 Posts
2 Delivery system
20 Delivery catheter
200 End cap
201 Lumen
21 Tethering member
210 End
211 Positive-locking member
212 Tether portion
22 Adapter piece
220 Body
221 Retainer groove
222 Recess
223 Slanted face
23 Mandrel
230 First portion
231 Second portion
232 Step
24 Handle device
240 Valve element
25 Security device
250 Housing body
251 Actuation member
252 Blocking opening
B Actuation direction
D Distal direction
F Pulling force
L Longitudinal axis
LA Left atrium
LV Left ventricle
M Intra-cardiac tissue (myocardium)
P Proximal direction
RA Right atrium
RV Right ventricle

The invention claimed is:

1. A delivery system for implanting a medical device, comprising:
   a leadless pacemaker device for providing a pacing of the heart's activity;
   a delivery catheter having an inner lumen,
   a mandrel received in the inner lumen of the delivery catheter and movable with respect to the delivery catheter,
   an adapter piece connected to the mandrel, wherein the adapter piece, by moving the mandrel with respect to the delivery catheter, is displaceable between a first position in which the adapter piece is received within the inner lumen of the delivery catheter and a second position in which the adapter piece is arranged outside of the inner lumen of the delivery catheter, and
   a tethering member comprising a tether portion having a first end at which the tethering member is connected to the adapter piece, the tether portion also having a second end spaced from the first end, wherein the tethering member further comprises a positive-locking member adjoining the tether portion at a distance from the first end, wherein the positive-locking member in a connection state is received on the adapter piece and is locked with respect to the adapter piece while the adapter piece is in the first position, and wherein the positive-locking member is releasable from the adapter piece by displacing the adapter piece from the first position towards the second position, and wherein when the positive-locking member is in the connection state, the tether portion in between the first end and the second end hence forms a loop such that by means of the tether portion a fixed connection of the leadless pacemaker to the delivery system is established.

2. The delivery system of claim 1, wherein the positive-locking member comprises a first diameter, measured along a plane perpendicular to a longitudinal axis of extension of the tethering member, larger than a second diameter of the tether portion.

3. The delivery system of claim 1, wherein the positive-locking member has a spherical shape.

4. The delivery system of claim 1, wherein the adapter piece comprises a body and a retainer groove formed on the body, wherein the tether portion in the connection state is received in the retainer groove.

5. The delivery system of claim 4, wherein the adapter piece comprises a recess formed on the body and adjoining the retainer groove, wherein the positive-locking member in the connection state is received in the recess.

6. The delivery system of claim 5, wherein the adapter piece is movable along a longitudinal direction between the first position and the second position with respect to the catheter device, wherein the recess is open at a lateral side of the adapter piece such that the positive-locking member is enabled to disengage from the recess in a direction transverse to the longitudinal direction if the adapter piece is in the second position, but is blocked from disengaging from the recess by the delivery catheter if the adapter piece is in the first position.

7. The delivery system of claim 5, wherein the adapter piece comprises a slanted face formed on the body at a transition between the recess and the retainer groove, wherein the slanted face is formed such that the positive-locking member is guided to release the tether portion from the retainer groove in case the locking of the positive-locking member with respect to the adapter piece is released and a pulling force (F) is exerted on the tether portion.

8. The delivery system of claim 5, further comprising a security device which is operatively connected to the mandrel, the security device being configured to prevent, in a first actuation state, a movement of the mandrel for releasing the positive-locking member from the adapter piece.

9. The delivery system of claim 8, wherein the security device comprises an actuation member which is actuatable for transferring the security device from the first actuation state to a second actuation state, the security device being configured to allow, in the second actuation state, a movement of the mandrel for releasing the positive-locking member from the adapter piece.

10. The delivery system of claim 8, wherein the security device comprises a housing body and a blocking opening formed therein through which the mandrel is passed, wherein the security device in the first actuation state blocks a movement of a portion of the mandrel through the blocking opening and in the second actuation state allows a movement of said portion of the mandrel through the blocking opening.

11. An assembly comprising a delivery system of claim 1 and a medical device having a housing and a connection member arranged on the housing, wherein the tether portion of the tethering member in the connection state is connected to the connection member.

12. The assembly of claim 11, wherein the connection member comprises an opening through which the tether portion extends in the connection state.

13. The assembly of claim 12, wherein the connection member comprises a shaft bordering the opening, wherein the tether portion in the connection state extends about the shaft.

14. The assembly of claim 13, wherein the connection member comprises a rounded face having, when viewed in a plane perpendicular to a longitudinal axis (L) of the shaft, a convex curvature, the rounded face bordering the opening at a side opposite the shaft.

15. A method for releasing a medical device from a delivery system, comprising:
providing the delivery system in a state in which the medical device is connected to the delivery system, the medical device comprising a leadless pacemaker device for providing a pacing of the heart's activity, the delivery system comprising a delivery catheter having an inner lumen, a mandrel received in the inner lumen of the delivery catheter and an adapter piece connected to the mandrel, wherein the adapter piece, by moving the mandrel with respect to the delivery catheter, is displaceable between a first position in which the adapter piece is received within the inner lumen of the delivery catheter and a second position in which the adapter piece is arranged outside of the inner lumen of the delivery catheter, wherein the delivery system further comprises a tethering member comprising a tether portion having a first end at which the tethering member is connected to the adapter piece, the tether portion also having a second end spaced from the first end, and the tethering member further comprises a positive-locking member adjoining the tether portion at a distance from the first end, wherein the positive-locking member in a connection state is received on the adapter piece and is locked with respect to the adapter piece while the adapter piece is in the first position, wherein the tether portion of the tethering member in the connection state is connected to a connection member of the medical device, wherein when the positive-locking member is in the connection state, the tether portion in between the first end and the second end hence forms a loop such that by means of the tether portion a fixed connection of the leadless pacemaker to the delivery system is established, and releasing the positive-locking member from the adapter piece by displacing the adapter piece from the first position towards the second position by moving the mandrel for disconnecting the connection member of the medical device from the tether portion.

* * * * *